(12) United States Patent
Bream et al.

(10) Patent No.: US 10,266,525 B2
(45) Date of Patent: Apr. 23, 2019

(54) PROCESSES FOR PREPARING 2-(6-(1H-INDOL-4-YL)-1H-INDAZOL-4-YL)-5-((4-ISOPROPYLPIPERAZIN-1-YL)METHYL)OXAZOLE

(71) Applicant: GlaxoSmithKline Intellectual Property Development Limited, Brentford, Middlesex (GB)

(72) Inventors: Robert Nicholas Bream, Stevenage (GB); John David Hayler, Stevenage (GB); Alan Geoffrey Ironmonger, Stevenage (GB); Peter Szeto, Stevenage (GB); Michael Robert Webb, Stevenage (GB); Katherine Marie Penelope Wheelhouse, Stevenage (GB); Robert David Willacy, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/578,258

(22) PCT Filed: May 31, 2016

(86) PCT No.: PCT/EP2016/062250
§ 371 (c)(1),
(2) Date: Nov. 30, 2017

(87) PCT Pub. No.: WO2016/193255
PCT Pub. Date: Dec. 8, 2016

(65) Prior Publication Data
US 2018/0155334 A1 Jun. 7, 2018

(30) Foreign Application Priority Data
Jun. 2, 2015 (GB) .................................. 1509492.3

(51) Int. Cl.
*C07D 231/56* (2006.01)
*C07D 413/14* (2006.01)
*C07D 263/32* (2006.01)
*C07F 5/02* (2006.01)

(52) U.S. Cl.
CPC ......... *C07D 413/14* (2013.01); *C07D 263/32* (2013.01); *C07F 5/02* (2013.01)

(58) Field of Classification Search
CPC .................................................... C07D 231/56
USPC ...................................................... 548/361.1
See application file for complete search history.

(56) References Cited

FOREIGN PATENT DOCUMENTS

WO 2012/032067 A1 3/2012
WO 2015/055691 A1 4/2015

*Primary Examiner* — Douglas M Willis
(74) *Attorney, Agent, or Firm* — Robert J. Smith

(57) ABSTRACT

The present invention provides novel processes for preparing compounds of formula (IV) and salts thereof

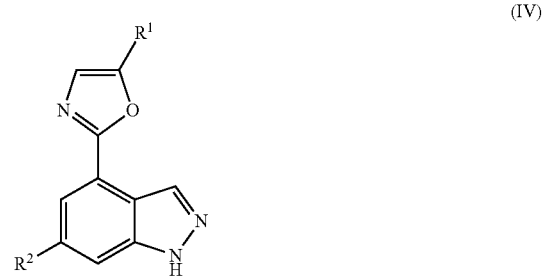

(IV)

novel intermediates, and a novel salt and polymorph thereof.

7 Claims, 1 Drawing Sheet

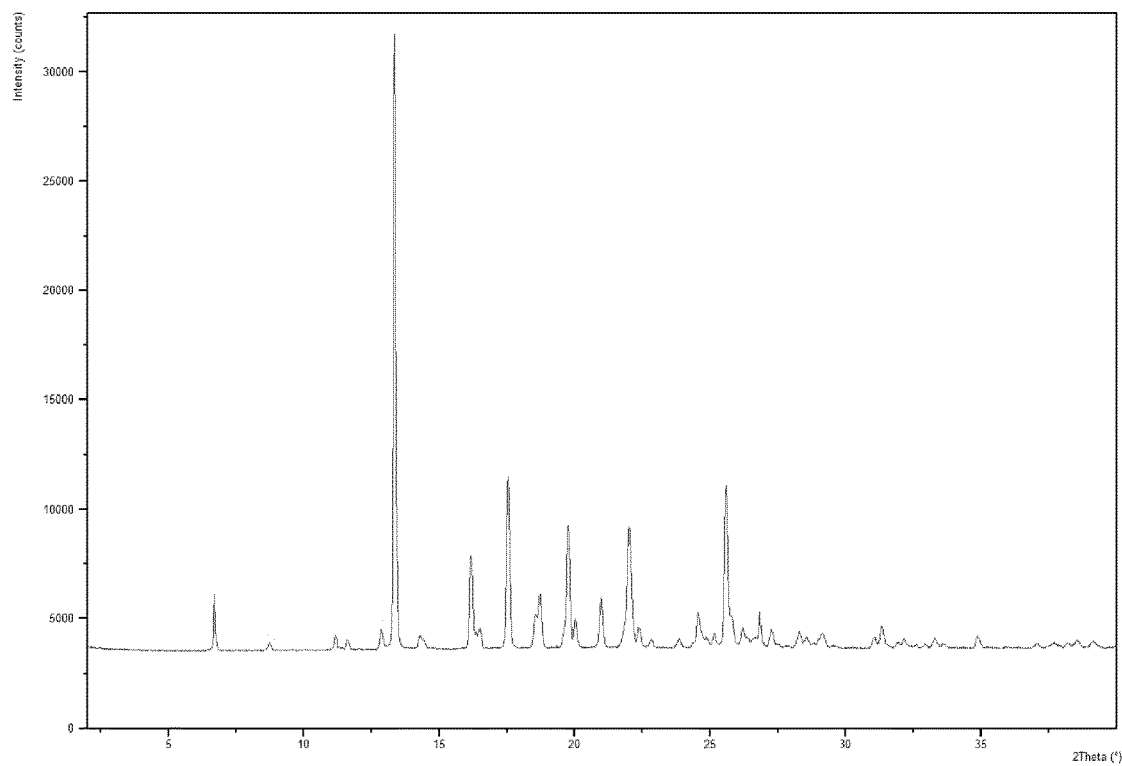

PROCESSES FOR PREPARING 2-(6-(1H-INDOL-4-YL)-1H-INDAZOL-4-YL)-5-((4-ISOPROPYLPIPERAZIN-1-YL)METHYL) OXAZOLE

This application is filed pursuant to 35 U.S.C. § 371 as a United States National Phase Application of International Patent Application Serial No. PCT/EP2016/062250 filed May 31, 2016, which claims priority of GB 1509492.3 filed 2 Jun. 2015.

FIELD OF THE INVENTION

The present invention is directed to novel processes for preparing compounds and salts thereof, which compounds are inhibitors of the activity or function of phosphoinositide 3'OH kinase isoform delta (PI3Kδ); novel intermediates; and a novel salt and polymorph thereof.

BACKGROUND TO THE INVENTION

International patent application PCT/EP2010/055666 (publication number WO2010/125082) describes compounds having the general formula (I):

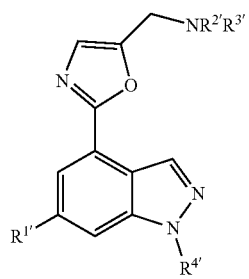

(I)

wherein
$R^{1'}$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —NHSO$_2$R$^{5'}$, or
pyridinyl optionally substituted by one or two substituents independently selected from $C_{1-6}$alkyl, —OR$^{6'}$, halo and —NHSO$_2$R$^{7'}$;
$R^{2'}$ and $R^{3'}$, together with the nitrogen atom to which they are attached, are linked to form a 6- or 7-membered heterocyclyl wherein the 6- or 7-membered heterocyclyl optionally contains an oxygen atom or a further nitrogen atom and is optionally substituted by one or two substituents independently selected from $C_{1-6}$alkyl;
$R^{4'}$ is hydrogen or methyl;
$R^{6'}$ is hydrogen or $C_{1-4}$alkyl; and
$R^{5'}$ and $R^{7'}$ are each independently $C_{1-6}$alkyl, or phenyl optionally substituted by one or two substituents independently selected from halo;
and salts thereof.

The examples of WO2010/125082 describe the preparation of 6-(1H-indol-4-yl)-4-(5-{[4-(1-methylethyl)-1-piperazinyl]methyl}-1,3-oxazol-2-yl)-1H-indazole which may be represented by the formula (II):

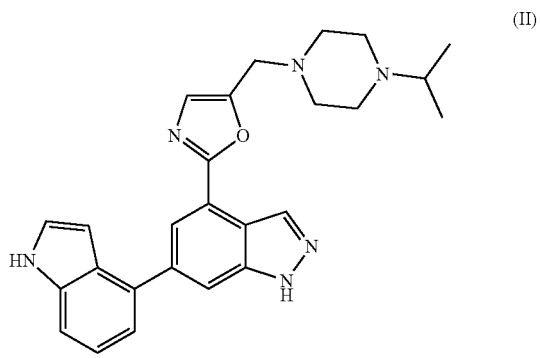 [SMILES: CC(C)N1CCN(Cc2cnc(-c3cc(-c4cccc5[nH]ccc45)cc4[nH]ncc34)o2)CC1]

hereinafter referred to as "Compound A" and the hydrochloride salts thereof, and the preparation of N-[5-[4-(5-{[(2R, 6S)-2,6-dimethyl-4-morpholinyl]methyl}-1,3-oxazol-2-yl)-1H-indazol-6-yl]-2-(methyloxy)-3-pyridinyl] methanesulfonamide which may be represented by the formula (III):

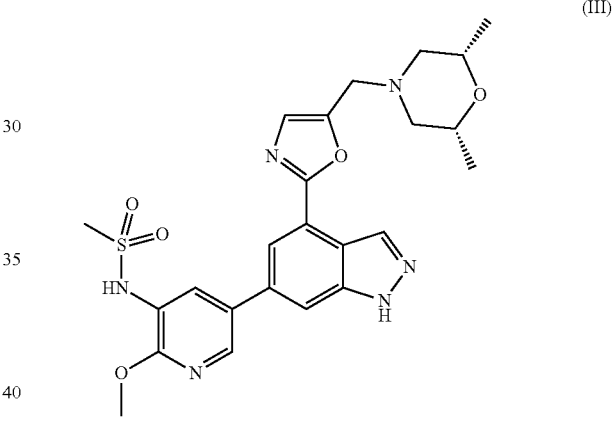

hereinafter referred to as "Compound B" and the (R)-mandelate salt thereof.

International patent application PCT/EP2011/068604 (publication number WO2012/055846) describes a novel polymorph of Compound A and salts of Compound A and polymorphs thereof, processes for their preparation, pharmaceutical compositions comprising them, and their use in the treatment of various disorders.

International patent application PCT/EP2011/065419 (publication number WO2012/032067) describes novel polymorphs and salts of Compound B, processes for their preparation, pharmaceutical compositions comprising them, and their use in the treatment of various disorders.

The processes for preparing Compounds A and B described in WO2010/125082, WO2012/055846 and WO2012/032067 are unsuitable for manufacturing the compounds on a commercial scale. For example, one of the methods described uses a stannane reagent in the key oxazole-indazole coupling step. Stannane reagents are typically toxic and environmentally harmful. An alternative process which avoids the use of a stannane reagent is described in WO2012/055846. However, this process requires a significant number of steps, starts from expensive starting materials and has a poor overall yield.

There therefore remains a need to develop an improved process for preparing Compounds A and B which may be suitable for use on a commercial scale.

SUMMARY OF THE INVENTION

The present invention provides novel processes for preparing compounds of formula (IV) and salts thereof wherein $R^1$ and $R^2$ are as defined below, novel intermediates, and a novel salt and polymorph thereof.

BRIEF DESCRIPTION OF THE FIGURES

FIG. 1 shows an X-ray powder diffraction (XRPD) pattern for a polymorph of 6-(1H-indol-4-yl)-4-(5-{[4-(1-methylethyl)-1-piperazinyl]methyl}-1,3-oxazol-2-yl)-1H-indazole benzoate.

DETAILED DESCRIPTION OF THE INVENTION

The present invention provides a number of aspects relating to a process which is summarised in Scheme 1 below:

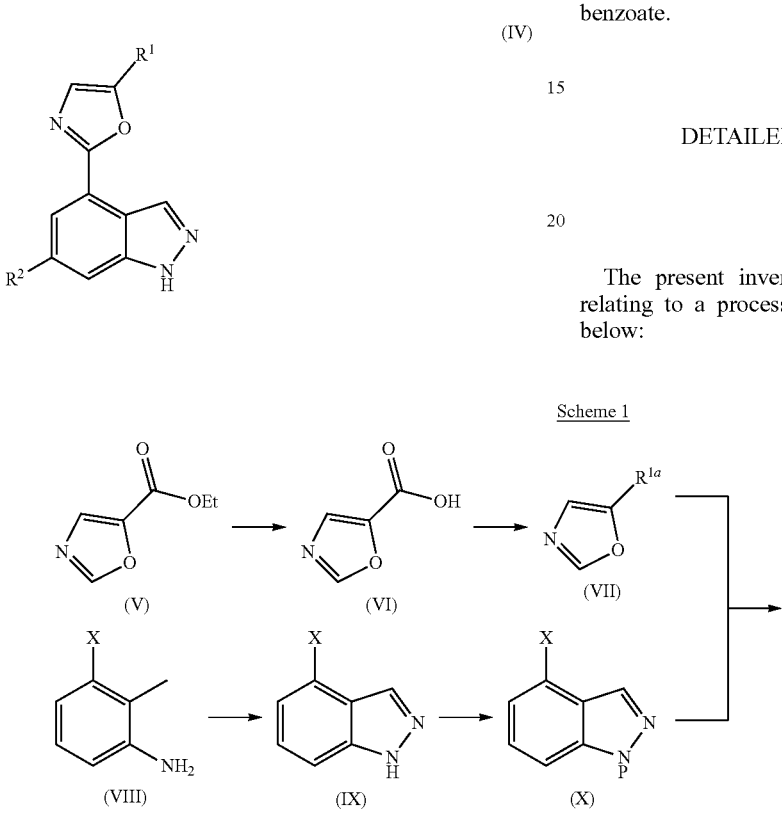

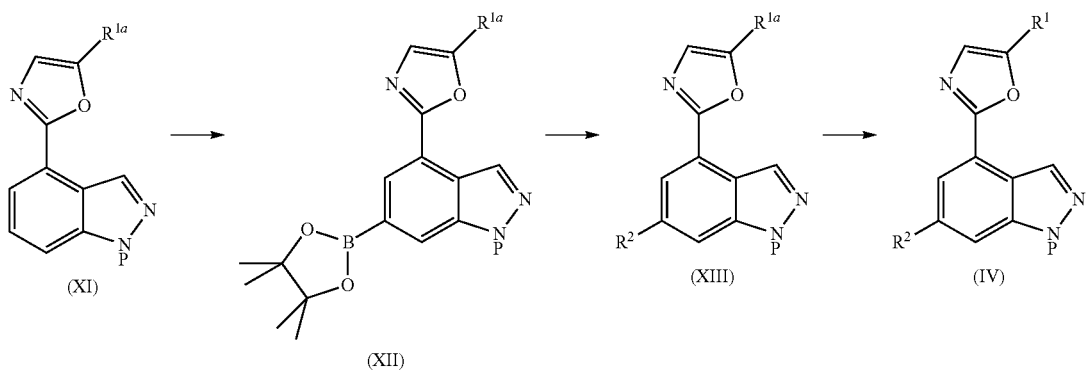

Thus, in one aspect, the present invention provides a process for preparing compounds of formula (IV) and salts thereof

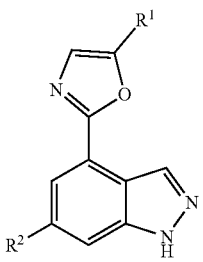
(IV)

wherein
R¹ is

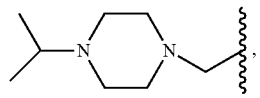

and
R² is

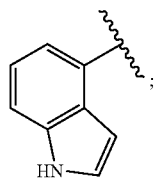 [SMILES: *c1cccc2[nH]ccc12]

or
R¹ is

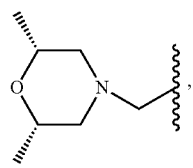

and
R² is

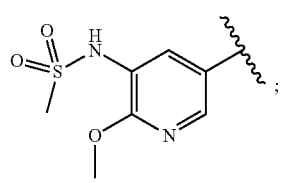 [SMILES: *c1cnc(OC)c(NS(C)(=O)=O)c1]

which process comprises:
(a) reacting a compound of formula (VII) or a salt thereof

(VII)

wherein R$^{1a}$ is

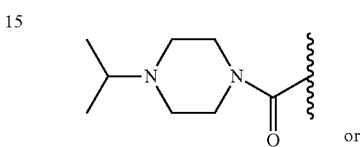
or

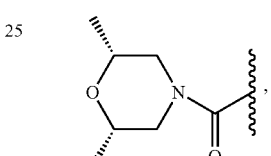

with a compound of formula (X) or a salt thereof

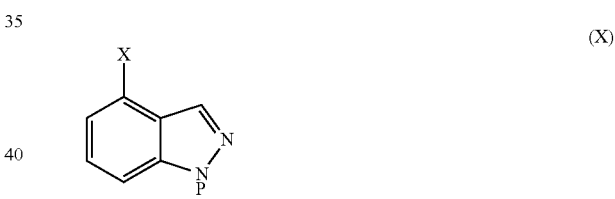
(X)

wherein X is halogen and P is a protecting group, in the presence of a palladium catalyst to give a compound of formula (XI) or a salt thereof

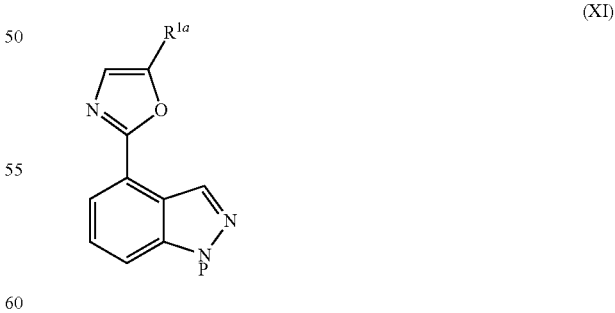
(XI)

wherein R$^{1a}$ and P are as defined above, followed by conversion of the compound of formula (XI) or a salt thereof to a compound of formula (IV) or a salt thereof, (b) reacting a compound of formula (XI) or a salt thereof with a borylating agent in the presence of a catalyst system to give a compound of formula (XII) or a salt thereof

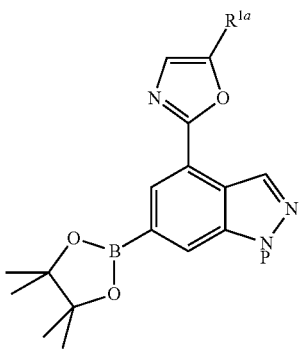

wherein $R^{1a}$ and P are as defined above, followed by conversion of the compound of formula (XII) or a salt thereof to a compound of formula (IV) or a salt thereof, (c) reacting a compound of formula (XII) or a salt thereof with a compound of formula (XIV) or a salt thereof $$R^2—X^1 \quad (XIV)$$

wherein $R^2$ is as defined above and $X^1$ is halogen, in the presence of a palladium catalyst to give a compound of formula (XIII) or a salt thereof

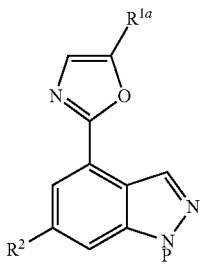

wherein $R^{1a}$, $R^2$ and P are as defined above, followed by conversion of the compound of formula (XIII) or a salt thereof to a compound of formula (IV) or a salt thereof, and/or (d) reacting a compound of formula (XIII) or a salt thereof with a reducing agent followed by deprotection.

The present invention provides processes for making compounds of formula IV comprising at least one of steps a to d. The processes of the present invention may include all four steps or one, two or three of steps a, b, c and d.

In one embodiment, $R^1$ is

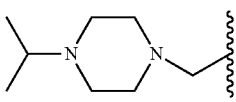

and $R^2$ is

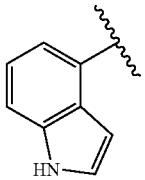 [SMILES: *c1cccc2[nH]ccc12]

such that the compound of formula (IV) or salt thereof produced by the process of the invention is Compound A or a salt thereof.

In a further embodiment, $R^1$ is

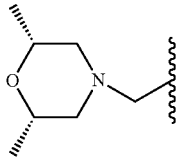 [SMILES: *CN1C[C@@H](C)O[C@@H](C)C1]

and $R^2$ is

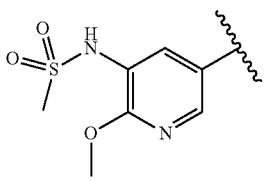 [SMILES: *c1cnc(OC)c(NS(C)(=O)=O)c1]

such that the compound of formula (IV) or salt thereof produced by the process of the invention is Compound B or a salt thereof.

Salts of Compounds A and B which may be prepared according to the invention include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate (for example the hemi fumarate), malate, tartrate, citrate, salicylate, p-aminosalicyclate, glycollate, lactate, heptanoate, phthalate, oxalate, succinate (for example the hemi succinate), benzoate, o-acetoxybenzoate, chlorobenzoate, methyl benzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate (for example the hemi pamoate), malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, naphthalenedisulfonate (for example the hemi naphthalenedisulfonate), mesitylenesulfonate, biphenyldisulfonate (for example the hemi biphenyldisulfonate), cinnamate (for example the hemi cinnamate), sebacate (for example the hemi sebacate), pyromellitate (for example the hemi pyromellitate) and benzenediacrylate (for example hemi benzenediacrylate salt).

In one embodiment, the process of the present invention may be used to prepare the hemi succinate salt of Compound A. In another embodiment, the process of the present invention may be used to prepare the benzoate salt of Compound A. The benzoate salt of Compound A has certain properties which may make it particularly suitable for development as an inhaled drug, in particular, it has suitable solubility in simulated lung fluid, good chemical and physical stability, and suitable hygroscopicity. Accordingly, 6-(1H-indol-4-yl)-4-(5-{[4-(1-methylethyl)-1-piperazinyl]methyl}-1,3-oxazol-2-yl)-1H-indazole benzoate forms a further aspect of the present invention.

Also included within the scope of the invention are any solvates, for example hydrates, complexes and polymorphic forms of 6-(1H-indol-4-yl)-4-(5-{[4-(1-methylethyl)-1-piperazinyl]methyl}-1,3-oxazol-2-yl)-1H-indazole benzoate. 6-(1H-Indol-4-yl)-4-(5-{[4-(1-methylethyl)-1-piperazinyl]methyl}-1,3-oxazol-2-yl)-1H-indazole benzoate may exist in crystalline or noncrystalline form, or as a mixture thereof. For salts that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. As the skilled person will appreciate, the amount of water may depend upon the conditions, for example humidity. For example, as humidity decreases the amount of water may decrease and as humidity increases the amount of water may increase. Such variations in the amount of water are included within the scope of the invention.

In one embodiment, the invention provides a polymorph of 6-(1H-indol-4-yl)-4-(5-{[4-(1-methylethyl)-1-piperazinyl]methyl}-1,3-oxazol-2-yl)-1H-indazole benzoate characterised in that it provides an XRPD pattern comprising peaks (° 2θ) at about 6.7 and/or about 8.7 and/or about 11.6 and/or about 12.9 and/or about 13.3 and/or about 16.2.

In one embodiment, the invention provides a polymorph of 6-(1H-indol-4-yl)-4-(5-{[4-(1-methylethyl)-1-piperazinyl]methyl}-1,3-oxazol-2-yl)-1H-indazole benzoate characterised in that it provides an XRPD pattern comprising peaks (° 2θ) at about 6.7, about 8.7, about 11.6, about 12.9, about 13.3 and about 16.2.

In another embodiment, the invention provides a polymorph of 6-(1H-indol-4-yl)-4-(5-{[4-(1-methylethyl)-1-piperazinyl]methyl}-1,3-oxazol-2-yl)-1H-indazole benzoate characterised in that it provides an XRPD pattern comprising peaks substantially as set out in Table 1.

In a further embodiment, the invention provides a polymorph of 6-(1H-indol-4-yl)-4-(5-{[4-(1-methylethyl)-1-piperazinyl]methyl}-1,3-oxazol-2-yl)-1H-indazole benzoate characterised in that it provides an XRPD pattern substantially in accordance with FIG. 1.

When it is indicated herein that there is a peak in an XRPD pattern at a given value, it is typically meant that the peak is within ±0.2 of the value quoted, for example within ±0.1 of the value quoted.

In another aspect, the present invention provides a process for preparing compounds of formula (XI) and salts thereof

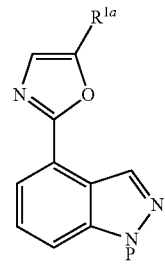

(XI)

wherein $R^{1a}$ is

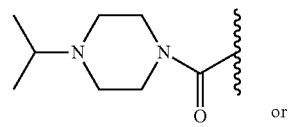

or

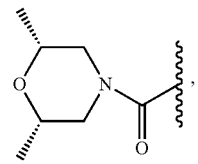

and P is a protecting group, which process comprises reacting a compound of formula (VII) or a salt thereof

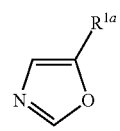

(VII)

wherein $R^{1a}$ is as defined above, with a compound of formula (X) or a salt thereof

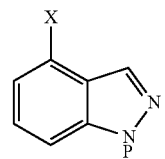

(X)

wherein X is halogen and P is as defined above, in the presence of a palladium catalyst.

In another aspect, the present invention provides a process for preparing compounds of formula (IV) and salts thereof

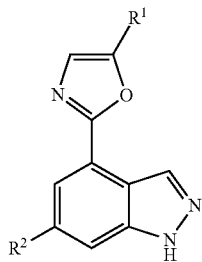

wherein
R¹ is

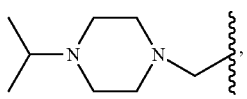 [SMILES: *CN1CCN(C(C)C)CC1]

and
R² is

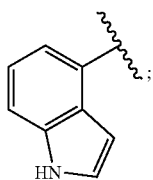

or
R¹ is

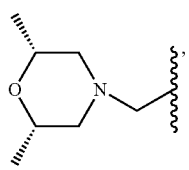

and
R² is

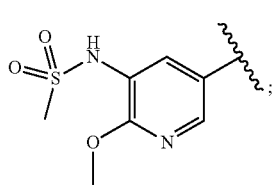 [SMILES: *c1cnc(OC)c(NS(C)(=O)=O)c1]

which process comprises reacting a compound of formula (VII) or a salt thereof

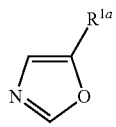

(VII)

wherein R¹ᵃ is as defined above, with a compound of formula (X) or a salt thereof

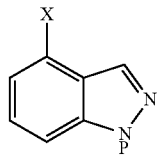

(X)

wherein X and P are as defined above, in the presence of a palladium catalyst to give a compound of formula (XI) or a salt thereof

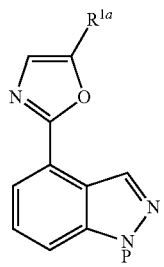

(XI)

wherein R¹ᵃ and P are as defined above, followed by conversion of the compound of formula (XI) or a salt thereof to a compound of formula (IV) or a salt thereof.

In one embodiment, R¹ᵃ is

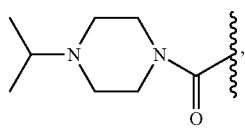

In a further embodiment, R¹ᵃ is

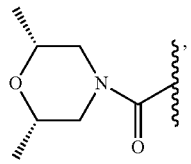 [SMILES: *C(=O)N1C[C@@H](C)O[C@@H](C)C1]

The protecting group P may be any suitable protecting group described in, for example, Protective Groups in Organic Synthesis by Wuts and Greene (John Wiley & Sons). In one embodiment, the protecting group is tetrahydro-2H-pyran-2-yl.

In one embodiment, X is chlorine. In a further embodiment, X is bromine.

The palladium catalyst used in the formation of the compound of formula (XI) described above may be any suitable palladium catalyst complex, for example a palladium complex with a suitable ligand. The ligand may be, for example, a Buchwald ligand such as XPhos (2-dicyclohexylphosphino-2',4',6'-triisopropylbiphenyl) or RuPhos (2-dicyclohexylphosphino-2',6'-diisopropoxybiphenyl). In one embodiment, the palladium catalyst is a palladium complex with XPhos.

The compound of formula (VII) or salt thereof may be prepared from ethyl oxazole-5-carboxylic acid, the compound of formula (V) or a salt thereof

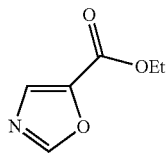
(V)

by hydrolysis to give oxazole-5-carboxylic acid, the compound of formula (VI) or a salt thereof

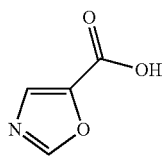
(VI)

followed by amination with 1-(isopropyl)piperazine or (2R, 6S)-2,6-dimethylmorpholine.

Alternatively, the compound of formula (VII) or a salt thereof may be prepared directly by treatment of ethyl oxazole-5-carboxylic acid with 1-(isopropyl)piperazine or (2R, 6S)-2,6-dimethylmorpholine in the presence of an enzyme. In one embodiment, the enzyme is lyophilised lipase TL.

The compound of formula (X) or salt thereof may be prepared by reacting a compound of formula (VIII) or a salt thereof

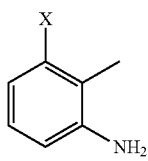
(VIII)

wherein X is as defined above, with isoamyl nitrite, followed by protection.

Alternatively, in another aspect, the present invention provides a process for preparing compounds of formula (XI) and salts thereof

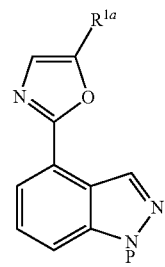
(XI)

wherein $R^{1a}$ is and P are as defined above, which process comprises reacting a compound of formula (Va) or a salt thereof

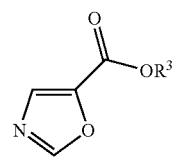
(Va)

wherein $R^3$ is $C_{1-6}$alkyl, such as ethyl (to give a compound of formula (V) as defined above), with a compound of formula (X) or a salt thereof

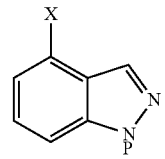
(X)

wherein X is halogen and P is as defined above, in the presence of a palladium catalyst, followed by hydrolysis and amination with 1-(isopropyl)piperazine or (2R, 6S)-2,6-dimethylmorpholine.

In another aspect, the present invention provides a process for preparing compounds of formula (IV) and salts thereof

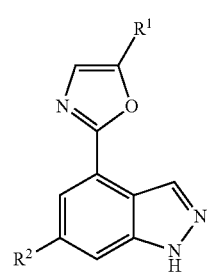
(IV)

wherein $R^1$ and $R^2$ are as defined above, which process comprises reacting a compound of formula (Va) or a salt thereof

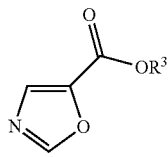
(Va)

wherein R³ is as defined above, with a compound of formula (X) or a salt thereof

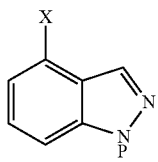
(X)

wherein X and P are as defined above, in the presence of a palladium catalyst, followed by hydrolysis and amination with 1-(isopropyl)piperazine or (2R, 6S)-2,6-dimethylmorpholine, to give a compound of formula (XI) or a salt thereof

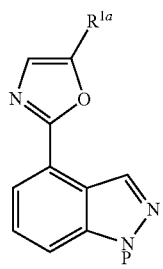
(XI)

wherein $R^{1a}$ and P are as defined above, followed by conversion of the compound of formula (XI) or a salt thereof to a compound of formula (IV) or a salt thereof.

In another aspect, the present invention provides a process for preparing compounds of formula (XII) and salts thereof

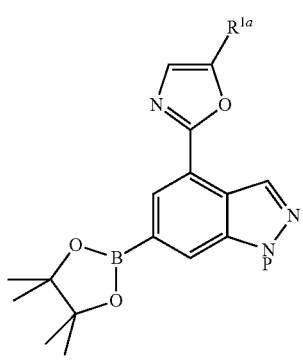
(XII)

wherein $R^{1a}$ and P are as defined above,
which process comprises reacting a compound of formula (XI) or a salt thereof

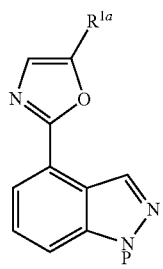
(XI)

wherein $R^{1a}$ and P are as defined above, with a borylating agent in the presence of a catalyst system.

In another aspect, the present invention provides a process for preparing compounds of formula (IV) and salts thereof

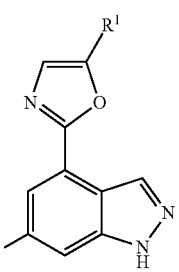
(IV)

wherein $R^1$ and $R^2$ are as defined above, which process comprises reacting a compound of formula (XI) or a salt thereof

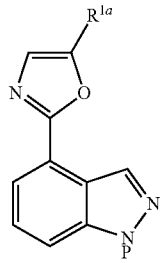
(XI)

wherein $R^{1a}$ and P are as defined above, with a borylating agent in the presence of a catalyst system to give a compound of formula (XII) or a salt thereof

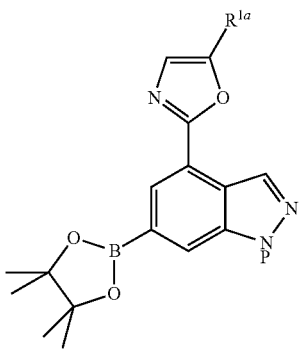

(XII)

wherein R¹ᵃ and P are as defined above, followed by conversion of the compound of formula (XII) or a salt thereof to a compound of formula (IV) or a salt thereof.

The borylating agent used according to the present invention may be any suitable borylating agent such as pinacolborane.

The catalyst system used according to the present invention may be any suitable catalyst system such as an iridium, nickel, iron, rhodium or cobalt catalyst system. Suitable catalyst systems are described in, for example, Chem. Commun., 2015, 51, 6508-6511; J. Am. Chem. Soc., 2013, 135, 17258-17261; and J. Am. Chem. Soc., 2014, 136, 4133-4136. In one embodiment, the catalyst system is an iridium catalyst system, for example, (1,5-cyclooctodiene)(methoxy)iridium (I) dimer.

In another aspect, the present invention provides a process for preparing compounds of formula (XIII) and salts thereof

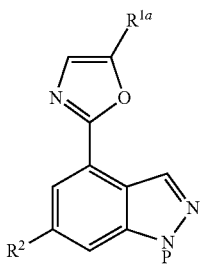

(XIII)

wherein R¹ᵃ, R² and P are as defined above,
which process comprises reacting a compound of formula (XII) or a salt thereof

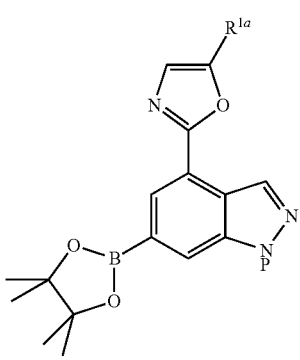

(XII)

wherein R¹ᵃ and P are as defined above, with a compound of formula (XIV) or a salt thereof

R²—X¹ (XIV)

wherein R² is as defined above and X¹ is halogen, in the presence of a palladium catalyst.

In another aspect, the present invention provides a process for preparing compounds of formula (IV) and salts thereof

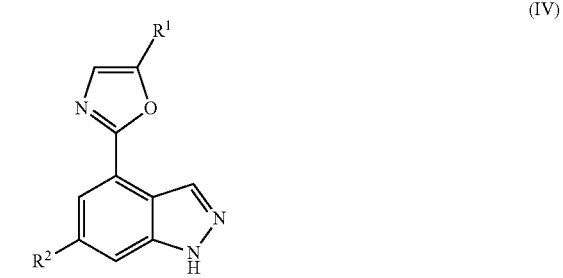

(IV)

wherein R¹ and R² are as defined above,
which process comprises reacting a compound of formula (XII)

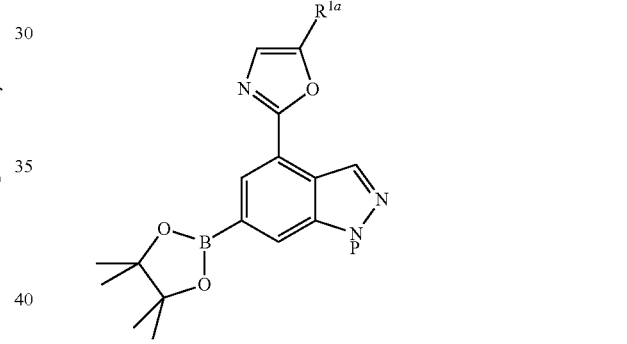

(XII)

wherein R¹ᵃ and P are as defined above, with a compound of formula (XIV)

R²—X¹ (XIV)

wherein R² is as defined above and X¹ is halogen, in the presence of a palladium catalyst to give a compound of formula (XIII)

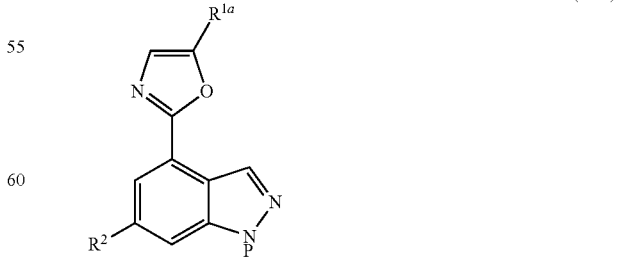

(XIII)

wherein R¹ᵃ, R² and P are as defined above, followed by conversion of the compound of formula (XIII) or a salt thereof to a compound of formula (IV) or a salt thereof.

In one embodiment, $X^1$ is chlorine. In a further embodiment, $X^1$ is bromine.

The palladium catalyst used in the formation of the compound of formula (XIII) described above may be any suitable palladium catalyst complex, for example a palladium complex with a suitable ligand. The ligand may be, for example, a Buchwald ligand such as XPhos (2-dicyclohexylphosphino-2',4',6'-triisopropylbiphenyl) or tricyclohexylphosphine. In one embodiment, the palladium catalyst is a palladium complex with XPhos.

In a further aspect, the present invention provides a process for preparing compounds of formula (IV) and salts thereof

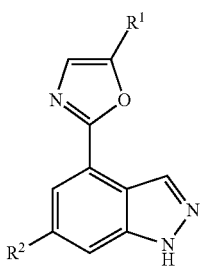

(IV)

wherein $R^1$ and $R^2$ are as defined above,
which process comprises reacting a compound of formula (XIII) or a salt thereof

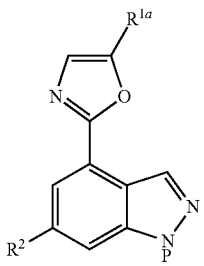

(XIII)

wherein $R^{1a}$, $R^2$ and P are as defined above, with a reducing agent followed by deprotection.

The reducing agent may be any suitable reducing agent such as a hydride, for example, lithium aluminium hydride, sodium borohydride, diisobutylaluminium hydride (DIBAL) or sodium bis(2-methoxyethoxy)aluminium hydride (Red-Al). In one embodiment, the reducing agent is lithium aluminium hydride.

As a person skilled in the art will appreciate, the conditions required for deprotection will depend on the nature of the protecting group. If the protecting group used is tetrahydro-2H-pyran-2-yl, it may be removed under acidic conditions. The intermediate compounds of formulae (VII), (XI), (XII) and (XIII) are novel and thus the compounds and their salts form another aspect of the invention.

In one embodiment, the present invention provides a compound of formula (VII) or a salt thereof wherein $R^{1a}$ is

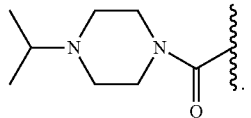

In another embodiment, the present invention provides a compound of formula (XI) or a salt thereof wherein $R^{1a}$ is

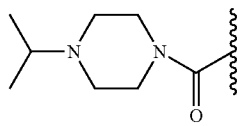

and P is tetrahydro-2H-pyran-2-yl.

In another embodiment, the present invention provides a compound of formula (XII) or a salt thereof wherein $R^{1a}$ is

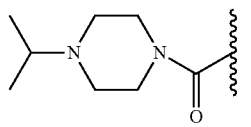 [SMILES: *C(=O)N1CCN(C(C)C)CC1]

and P is tetrahydro-2H-pyran-2-yl.

In another embodiment, the present invention provides a compound of formula (XIII) or a salt thereof wherein $R^{1a}$ is

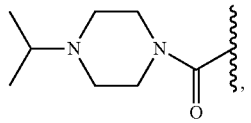 [SMILES: *C(=O)N1CCN(C(C)C)CC1]

$R^2$ is

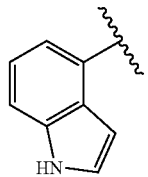 [SMILES: *c1cccc2[nH]ccc12]

and P is tetrahydro-2H-pyran-2-yl.

A particular embodiment of the present invention is shown in Scheme 2 below and is described in detail in the following Examples, which are intended for illustration only and are not intended to limit the scope of the invention in any way.

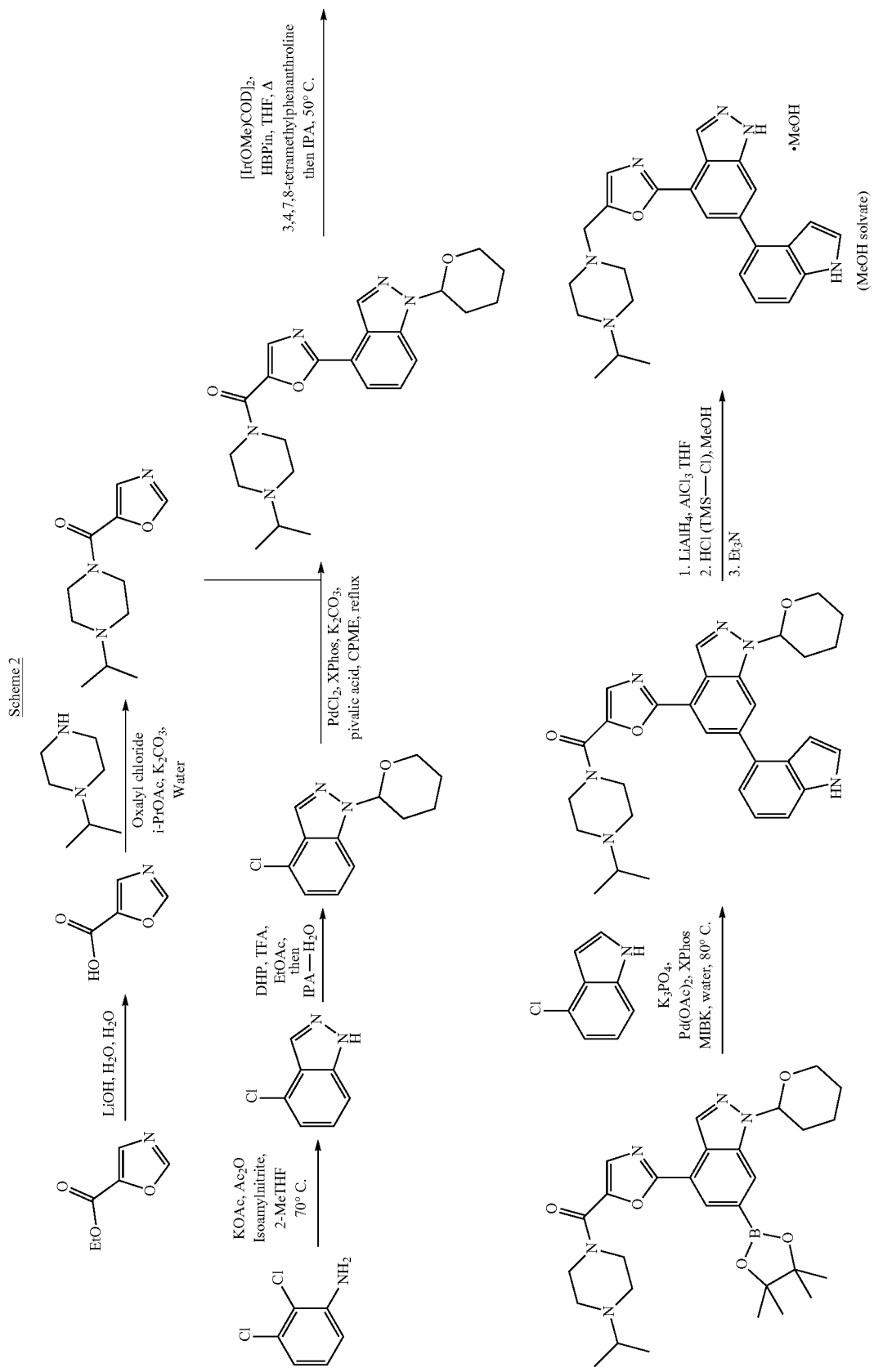

As used herein the symbols and conventions used in these processes, schemes and examples are consistent with those used in the contemporary scientific literature, for example, the *Journal of the American Chemical Society* or the *Journal of Biological Chemistry*. Unless otherwise noted, all starting materials were obtained from commercial suppliers and used without further purification. Specifically, the following abbreviations may be used in the examples and throughout the specification:

Ac Acetyl
COD 1,5-Cyclooctadiene
CPME Cyclopentyl methyl ether
DHP 3,4-Dihydro-2H-pyran
DMSO Dimethyl sulphoxide
Et Ethyl
EtOAc Ethyl acetate
g Grams
h Hour(s)
IPA isopropanol
iPr isopropyl
HPLC High performance liquid chromatography
kg kilograms
L Liter
Me Methyl
Mg Milligrams
MIBK Methyl isobutyl ketone
Min Minute(s)
ml Milliliters
mol Moles
mmol Millimoles
Pin Pinacol
RuPhos 2-dicyclohexylphosphino-2',6'-diisopropoxybiphenyl
Rt Retention time
TFA Trifluoroacetic acid
THF Tetrahydrofuran
TMS Trimethylsilane
XPhos 2-dicyclohexylphosphino-2',4',6'-triisopropylbiphenyl
XRPD X-ray powder diffraction

EXAMPLES

Intermediate 1

Oxazole-5-carboxylic Acid

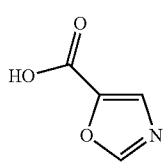

An aqueous solution of lithium hydroxide monohydrate (124.5 kg of a solution prepared from 49.44 kg lithium hydroxide monohydrate dissolved in 319 kg water, 398 mol) was added to a solution of ethyl 5-oxazolecarboxylate (54 kg, 382.7 mol) in water (54 kg) maintaining the temperature below 25° C. The reaction was stirred for 6.5 h and then conc. aqueous HCl (64.8 kg) was added maintaining the temperature below 25° C., the crystallisation cooled to 5° C. and held for 1 h. The product was filtered off, washed with cold water (88 kg), then isopropanol (171 kg) and dried under vacuum at 50° C. to give the title compound (37.88 kg, 87.5%).

$^1$H NMR (400 MHz, DMSO-$d_6$) δ ppm 13.68 (br. s., 1H), 8.59 (s, 1H), and 7.88 (s, 1H).

Intermediate 2

(4-Isopropylpiperazin-1-yl)(oxazol-5-yl)methanone

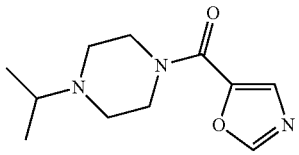 [SMILES: CC(C)N1CCN(C(=O)c2cnco2)CC1]

Method A

Oxalyl chloride (47.7 kg, 375.8 mol) was added to a solution of oxazole-5-carboxylic acid (32.88 kg, 290.8 mol) in isopropyl acetate (144 kg) maintaining the temperature at 52-58° C. The temperature was increased to 58.5° C., stirred for 5 h and then cooled to 20° C. The reaction mixture was added to a solution of 1-(isopropyl)piperazine (41 kg, 319.8 mol) and potassium carbonate (118.4 kg) in isopropyl acetate (348 kg) and water (103 kg) maintaining the temperature below 25° C. The reaction was stirred for 15 mins, the temperature was increased to 33° C. and the organic phase washed with water (191 kg), concentrated under reduced pressure to 95 L and cooled to 20° C. n-Heptane (157 kg) was added and the crystallisation stirred for 2 h, and the product filtered off, washed with n-heptane (157 kg) and dried under vacuum 40° C. to give the title compound (57.14 kg, 88.0%).

$^1$H NMR (400 MHz, CDCl$_3$-d) δ ppm 7.94 (s, 1H), 7.56 (s, 1H), 3.91-3.73 (m, 4H), 2.75 (spt., J=6.5 Hz, 1H), 2.63-2.52 (m, 4H) and 1.06 (d, J=6.6 Hz, 6H).

Method B

1-Isopropylpiperazine (1.06 g, 8.24 mmol) and ethyl-oxazole-5-carboxylate (1.16 g, 8.24 mmol) were added to a suspension of 5 Å molecular sieves (8.0 g) in cyclopentyl methyl ether (40 mL) and stirred for 1 h at 55° C. Lyophilised lipase TL (2.0 g) was added, the reaction mixture stirred for 28.75 h, then filtered through glass fibre paper, washed through with cyclopentyl methyl esther (3×6 mL). The combined filtrate and washings were concentrated under reduced pressure and the crude residue re-slurried in methyl cyclohexane (6 mL), filtered off, washed with methyl cyclohexane (2×5 mL), and dried under vacuum to give the title compound (1.40 g, 76%).

Intermediate 3

4-Chloro-1H-indazole

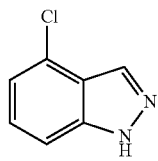

Acetic anhydride (69 kg, 675.9 mol) was added to a stirred slurry of 3-chloro-2-methylaniline (30 kg, 211.9 mol), potassium acetate (25 kg, 254.7 mol) and methyltetrahydrofuran (302 L) at 25° C. and then stirred for 2 h. Isopentyl nitrite (44.5 kg, 379.9 mol) was added to the slurry and the contents were heated to 73° C. for 18 h. The slurry was cooled to 20° C., then water (90 L) was added, and the reaction was cooled to 5° C. An aqueous solution of NaOH (105 L of a 32% w/w) was added, the solution was heated to 40° C. and stirred for 2 h. The lower aqueous phase was removed and the organic layer washed with water (150 L) and then brine (18 kg in 90 L water). The organic layer was concentrated to 90 L by atmospheric distillation and a solvent exchange to n-heptane performed by atmospheric distillation to a final volume of 240 L. The slurry was cooled to 7° C., stirred for 2 h and solid isolated by filtration. The cake was washed with heptane (2×60 L) and dried under vacuum to give the title compound (23.6 kg, 73%).

$^1$H NMR (400 MHz, MeOD-d$_4$) δ=8.08 (s, 1H), 7.48 (d, J=8.6 Hz, 1H), 7.33 (dd, J=7.5, 8.4 Hz, 1H), 7.14 (d, J=7.3 Hz, 1H)

HPLC r.t—1.94 min.

Intermediate 4

4-Chloro-1-(tetrahydro-2H-pyran-2-yl)-1H-indazole

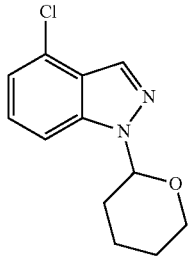 [SMILES: Clc1cccc2c1cnn2C1CCCCO1]

Trifluoroacetic acid (3.5 kg, 30.7 mol) was added to a solution of 4-chloro-1H-indazole (23 kg, 15.1 mol) and 3,4-dihydro-2H-pyran (43.1 kg, 512.7 mol) in ethyl acetate (235 L). The reaction mixture was heated to 80° C. for 4 h, then cooled to 23° C., triethylamine (3.2 kg, 31.6 mol) added and stirred for 30 min. The solvent was exchanged to isopropanol using an atmospheric distillation to a final volume of 138 L. The solution was cooled to 55° C. and water (138 L) was added maintaining the temperature. The solution was cooled to 42° C. and seeded (8 g), then cooled to 30° C., held for 10 h, and water (46 L) added, cooled to 18° C., and the slurry was stirred for 2 h then filtered off, washed with 6:1 v/v water/2-propanol (2×46 L) and dried under vacuum at 50° C. to give the title compound (28.8 kg, 80.7%).

$^1$H NMR (500 MHz, DMSO-d$_6$) δ=8.18 (s, 1H), 7.74 (d, J=8.5 Hz, 1H), 7.42 (dd, J=7.5, 8.4 Hz, 1H), 7.27 (d, J=7.3 Hz, 1H), 5.88 (dd, J=2.5, 9.5 Hz, 1H), 3.90-3.85 (m, 1H), 3.79-3.70 (m, 1H), 2.44-2.35 (m, 1H), 2.07-1.95 (m, 2H), 1.81-1.69 (m, 1H), 1.64-1.53 (m, 2H).

Intermediate 5

(4-Isopropylpiperazin-1-yl)(2-(1-(tetrahydro-2H-pyran-2-yl)-1H-indazol-4-yl)oxazol-5-yl)methanone

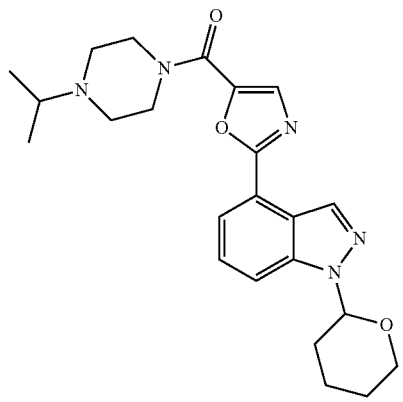 [SMILES: CC(C)N1CCN(C(=O)c2cnc(-c3cccc4c3cnn4C3CCCCO3)o2)CC1]

Method A

Palladium chloride (0.74 kg, 4.2 mol) and XPhos (4.36 kg, 9.1 mol) was suspended in cyclopentyl methyl ether (372 L). 4-Chloro-1-(tetrahydro-2H-pyran-2-yl)-1H-indazole (36 kg, 152.1 mol), (4-Isopropylpiperazin-1-yl)(oxazol-5-yl) methanone (34.78 kg, 155.8 mol) and potassium carbonate (325 mesh, 35.64 kg, 257.9 mol) were added and rinsed in with cyclopentyl methyl ether (2.58 kg). A solution of pivalic acid (9.294 kg, 91.0 mol) dissolved in cyclopentyl methyl ether (10 L) was added followed by a rinse of cyclopentyl methyl ether (10 L). The reaction was vacuum degassed and back-filled with nitrogen three times, then heated to reflux for 5 h and the contents cooled to 40° C. The reaction mixture was washed with water (144 L) then 5% w/v aqueous sodium chloride solution (151.2 kg) and the organic phase was concentrated at atmospheric pressure to 288 L. The reaction mixture was filtered into another vessel and the filter washed with cyclopentyl methyl ether (36 L), then distilled to 108 L under atmospheric pressure. Methyl cyclohexane (162 L) was added to the vessel maintaining the temperature at 75° C., the contents were then cooled to 62-65° C. and the crystallisation seeded with (4-isopropylpiperazin-1-yl)(2-(1-(tetrahydro-2H-pyran-2-yl)-1H-indazol-4-yl)oxazol-5-yl)methanone (90 g) slurried in chilled methyl cyclohexane (0.52 L). The crystallisation was held at 62° C. for 30 mins, cooled to 7° C. and then held at 7° C. overnight. The product was filtered off, washed with methyl cyclohexane (2×72 L) and dried in a vacuum oven at 50° C. to give the title compound (57.2 kg, 88.9%).

$^1$H NMR (400 MHz, DMSO-d$_6$) δ ppm 8.59 (s, 1H), 8.00 (d, J=8.6 Hz, 1H), 7.95 (s, 1H), 7.91 (d, J=7.3 Hz, 1H), 7.62 (dd, J=7.3, 8.3 Hz, 1H), 5.97 (dd, J=2.0, 9.5 Hz, 1H), 4.03-3.85 (m, 1H), 3.84-3.70 (m, 1H), 3.66 (br. s., 4H), 2.72 (spt., J=6.5 Hz, 1H), 2.57-2.40 (m, 5H), 2.11-1.96 (m, 2H), 1.85-1.68 (m, 1H), 1.68-1.47 (m, 2H), 0.99 (d, J=6.4 Hz, 6H)

Method B

4-Chloro-1-(tetrahydro-2H-pyran-2-yl)-1H-indazole (10 g, 42.2 mmol), (4-Isopropylpiperazin-1-yl)(oxazol-5-yl) methanone (9.67 g, 43.3 mmol), potassium carbonate (325 mesh, 9.93 g, 71.8 mmol) and pivalic acid (2.59 g, 25.3 mmol) were suspended in CPME (90 mL). The reaction was stirred for 10 mins at room temperature and then vacuum degassed and back-filled with nitrogen three times. Palladium chloride (206 mg, 1.16 mmol) and XPhos (1.21 g, 2.53 mmol) were added and rinsed in with CPME (10 mL). The reaction mixture was vacuum degassed and back-filled with nitrogen three times, then heated to reflux for 5 h and the contents cooled back to 50° C. The reaction mixture was washed with 3% w/w aqueous sodium chloride solution (30 mL), then 20% w/w aqueous sodium chloride solution (30 mL) and the organic phase was concentrated at atmospheric pressure down to 80 mL. The reaction mixture was cooled to room temperature and held overnight. The reaction mixture was then filtered into another vessel and the filter washed with CPME (20 mL), then distilled down to 30 mL under atmospheric pressure. The contents were cooled to 80° C. and methyl cyclohexane (45 mL) was added to the vessel maintaining the temperature at 75° C., the contents were then cooled to 62-65° C. and the crystallisation seeded with (4-isopropylpiperazin-1-yl)(2-(1-(tetrahydro-2H-pyran-2-yl)-1H-indazol-4-yl)oxazol-5-yl)methanone. The crystallisation was held at 63° C. for 30 mins, cooled to 5° C. over 6 h and then held at 5° C. overnight. The product was filtered off, washed with chilled methyl cyclohexane (2×20 mL) and dried in a vacuum oven at 50° C. to give the title compound (13.52 g, 76%).

$^1$H NMR (400 MHz, DMSO-$d_6$) δ ppm 8.59 (s, 1H), 8.00 (d, J=8.6 Hz, 1H), 7.95 (s, 1H), 7.91 (d, J=7.3 Hz, 1H), 7.62 (dd, J=7.3, 8.3 Hz, 1H), 5.97 (dd, J=2.0, 9.5 Hz, 1H), 4.03-3.85 (m, 1H), 3.84-3.70 (m, 1H), 3.66 (br. s., 4H), 2.72 (spt., J=6.5 Hz, 1H), 2.57-2.40 (m, 5H), 2.11-1.96 (m, 2H), 1.85-1.68 (m, 1H), 1.68-1.47 (m, 2H), 0.99 (d, J=6.4 Hz, 6H)

Intermediate 6

(4-Isopropylpiperazin-1-yl)(2-(1-(tetrahydro-2H-pyran-2-yl)-6-(4,4,5,5-tetramethyl-1,3,2-dioxaborolan-2-yl)-1H-indazol-4-yl)oxazol-5-yl)methanone

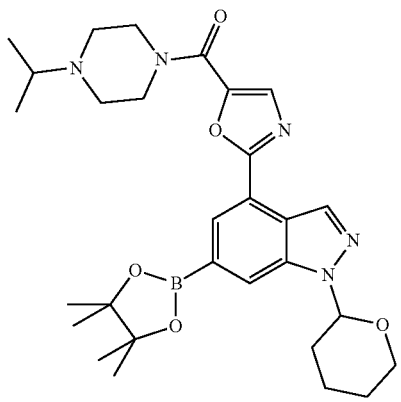 [SMILES: CC(C)N1CCN(C(=O)c2cnc(-c3cc(B4OC(C)(C)C(C)(C)O4)cc4c3cnn4C3CCCCO3)o2)CC1]

Pinacolborane (40.80 kg, 318.8 mol) was added to a stirred solution of (4-isopropylpiperazin-1-yl)(2-(1-(tetrahydro-2H-pyran-2-yl)-1H-indazol-4-yl)oxazol-5-yl)methanone (54.00 kg, 127.5 mol), (1,5-cyclooctadiene)(methoxy)iridium(I) dimer (0.864 kg, 1.30 mol) and 3,4,7,8-tetramethyl-1,10-phenanthroline (1.51 kg, 6.39 mol) in THF (243.2 kg) at 20° C. The reaction was heated to reflux for 8 h, then cooled to 20° C. and transferred into a vessel containing isopropanol (253.8 kg), washed through with THF (23.8 kg). The solvent was distilled to 270 L at 200 mbar and isopropanol (253.8 kg) was added and then redistilled to 324 L at 100 mbar. The crystallisation is heated to 40° C. for 4 h, cooled to 20° C., stirred overnight, filtered off, washed with isopropanol (84.8 kg), and dried in a vacuum oven at 50° C. to give the title compound (57.35 kg, 82.8%).

$^1$H NMR (400 MHz, CDCl$_3$-d) δ ppm 8.70 (s, 1H), 8.40 (s, 1H), 8.17 (s, 1H), 7.74 (s, 1H), 5.85 (dd, J=2.4, 9.5 Hz, 1H), 4.11-4.03 (m, 1H), 3.97-3.77 (m, 5H), 2.78 (spt., J=6.4 Hz, 1H), 2.70-2.59 (m, 5H), 2.24-2.14 (m, 1H), 2.14-2.03 (m, 1H), 1.86-1.72 (m, 2H), 1.72-1.62 (m, 1H), 1.40 (s, 12H), 1.08 (d, J=6.4 Hz, 6H).

Intermediate 7

(2-(6-(1H-indol-4-yl)-1-(tetrahydro-2H-pyran-2-yl)-1H-indazol-4-yl)oxazol-5-yl)(4-isopropylpiperazin-1-yl)methanone

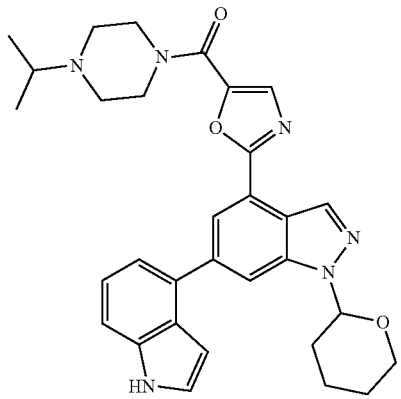 [SMILES: CC(C)N1CCN(C(=O)c2cnc(-c3cc(-c4cccc5[nH]ccc45)cc4c3cnn4C3CCCCO3)o2)CC1]

Method A

4-Chloroindole (13.8 kg, 91.04 mol) was added to a stirred solution of (4-isopropylpiperazin-1-yl)(2-(1-(tetrahydro-2H-pyran-2-yl)-6-(4,4,5,5-tetramethyl-1,3,2-dioxaborolan-2-yl)-1H-indazol-4-yl)oxazol-5-yl)methanone (50 kg, 91.00 mol), palladium acetate (0.2 kg, 0.89 mol), XPhos (0.65 kg, 1.36 mol), and potassium phosphate (46.4 kg, 218.6 mol) in MIBK (176 kg) and water (250 kg). The reaction mixture was degassed under vacuum 3×, then heated to 82° C. for 78 mins, and MIBK (300 L) added. The phases were mixed for 30 mins, then separated and the organic phase washed with an aqueous solution made up from potassium carbonate (2.75 kg), N-acetyl cysteine (5.2 kg) and water (250 kg), then water (250 kg) and distilled down to 300 L at atmospheric pressure. The crystallisation was cooled to 20° C., stirred for 5 h, filtered off, washed with MIBK (80 kg) and dried in the vacuum oven at 50° C. to give the title compound (36.15 kg, 73.7%).

$^1$H NMR (400 MHz, CDCl$_3$-d) δ ppm 8.72 (s, 1H), 8.38 (br. s, 1H), 8.35 (d, J=1.0 Hz, 1H), 8.06 (s, 1H), 7.81 (s, 1H), 7.52-7.46 (m, 1H), 7.36-7.30 (m, 3H), 6.79-6.75 (m, 1H), 5.84 (dd, J=9.17, 2.32 Hz, 1H), 4.10-4.04 (m, 1H), 3.88 (br. s., 4H), 3.84-3.72 (m, 1H), 2.76 (spt., J=6.5 Hz, 1H), 2.68-2.59 (m, 5H), 2.30-2.12 (m, 2H), 1.86-1.73 (m, 2H), 1.73-1.64 (m, 1H), 1.07 (d, J=6.60 Hz, 6H).

Method B

4-Chloroindole (8.71 kg, 57.46 mol) was added to a stirred solution of (4-isopropylpiperazin-1-yl)(2-(1-(tetrahydro-2H-pyran-2-yl)-6-(4,4,5,5-tetramethyl-1,3,2-dioxaborolan-2-yl)-1H-indazol-4-yl)oxazol-5-yl)methanone (34.55 kg, 62.88 mol), and potassium phosphate (32.1 kg, 151.2 mol) in MIBK (139.2 kg) and water (172.8 kg). The reaction mixture was degassed under vacuum 3×, and then palladium acetate (0.14 kg, 0.62 mol) and XPhos (0.45 kg, 0.94 mol) were added rinsed in with MIBK (1 kg). The reaction was heated to reflux for 1 h. The reaction was cooled to less than 40° C. and N-acetyl cysteine (3.59 kg) added, followed by MIBK (138.2 kg). The phases were heated to 82° C., mixed, then separated and the organic phase washed with an aqueous solution made up from potassium carbonate (1.9 kg), N-acetyl cysteine (3.59 kg), MIBK (27.6 kg) and water (173.8 kg), then water (172.8 kg) and distilled down to 155 L at atmospheric pressure. The crystallisation was cooled to 20° C., stirred for 22 h, filtered off, washing with MIBK (2×55.3 kg) and dried in a vacuum oven at 50° C. to give the title compound 24.72 kg, 73%).

$^1$H NMR (400 MHz, CDCl$_3$-d) δ ppm 8.72 (s, 1H), 8.38 (br. s, 1H), 8.35 (d, J=1.0 Hz, 1H), 8.06 (s, 1H), 7.81 (s, 1H), 7.52-7.46 (m, 1H), 7.36-7.30 (m, 3H), 6.79-6.75 (m, 1H), 5.84 (dd, J=9.17, 2.32 Hz, 1H), 4.10-4.04 (m, 1H), 3.88 (br. s., 4H), 3.84-3.72 (m, 1H), 2.76 (spt., J=6.5 Hz, 1H), 2.68-2.59 (m, 5H), 2.30-2.12 (m, 2H), 1.86-1.73 (m, 2H), 1.73-1.64 (m, 1H), 1.07 (d, J=6.60 Hz, 6H).

Example 1

2-(6-(1H-Indol-4-yl)-1H-indazol-4-yl)-5-((4-isopropylpiperazin-1-yl)methyl)oxazole methanol Solvate Method A Aluminium chloride (2.94 kg, 22 mol) was added to THF (216 kg) and stirred until dissolved. (2-(6-(1H-Indol-4-yl)-1-(tetrahydro-2H-pyran-2-yl)-1H-indazol-4-yl)oxazol-5-yl)(4-isopropylpiperazin-1-yl)methanone (34.75 kg, 64.5 mol) was added to the vessel washed in with THF (0.5 kg) and the contents cooled to 0° C. A solution of lithium aluminium hydride in THF (10% w/w, 22.6 kg, 59.6 mol) was added maintaining the temperature at less than 20° C., followed by a THF (0.9 kg) line wash. The reaction was stirred for 30 mins and then EtOAc (15.6 kg) added followed by a 1 h stir. A solution of triethanolamine (2.36 kg) in THF (2.1 L) was added followed by triethanolamine (36.8 kg) and then aqueous NaOH (15% w/w, 121 kg). The phases were separated and the organic phase washed with aqueous NaOH (15% w/w, 121 kg), THF (17 kg) added, and the solvent distilled down to 104 L at atmospheric pressure. A constant volume distillation (104 L) was performed by adding MeOH (174 L), and then MeOH (193.3 kg) added. Chlorotrimethylsilane (35.8 kg, 329.5 mol) was added and the reaction heated to 50° C. for 3 h, and then triethylamine (35.8 kg, 353.8 mol) added and the crystallisation cooled to 20° C., filtered off, washed with MeOH (2×55 kg) and dried in the vacuum oven at 50° C. to give the title compound (24.80 kg, 81%).

$^1$H NMR (400 MHz, DMSO-d$_6$) δ ppm 13.43 (br. s., 1H), 11.36 (br. s., 1H), 8.61 (s, 1H), 8.09 (d, J=1.2 Hz, 1H), 7.92 (m, 1H), 7.51-7.46 (m, 2H), 7.32 (s, 1H), 7.28-7.22 (m, 2H), 6.61 (m, 1H), 4.09 (q, J=5.3 Hz, 1H), 3.73 (s, 2H), 3.18 (d, J=4.9 Hz, 3H), 2.60 (br. s., 1H), 2.56-2.40 (m, 4H), 0.94 (d, J=6.4 Hz, 6H).

Method B

Aluminium chloride (4.25 g, 31.8 mmol) was added to THF (250 mL) and stirred until dissolved. (2-(6-(1H-Indol-4-yl)-1-(tetrahydro-2H-pyran-2-yl)-1H-indazol-4-yl)oxazol-5-yl)(4-isopropylpiperazin-1-yl)methanone (50 g, 93 mmol) was added to the vessel washed in with THF (100 mL) and the contents cooled to 0-5° C. A solution of lithium aluminium hydride in THF (10% w/w, 35.6 mL, 85 mmol) was added maintaining the temperature at less than 20° C.

The reaction was stirred for 105 mins and then EtOAc (25 mL) added followed by a 1 h stir. Triethanolamine (50.5 mL) was added followed aqueous NaOH (15% w/w, 150 mL). The phases were separated and the organic phase washed with aqueous NaOH (15% w/w, 150 mL), and the solvent distilled down to 150 mL at atmospheric pressure. A constant volume distillation (150 mL) was performed by adding MeOH (250 mL). In a separate vessel, chlorotrimethylsilane (59.3 mL, 464 mol) was added cautiously to MeOH (400 mL). The reaction was heated to 50-55° C. and the methanol solution of the substrate was added over approximately 2 h. The reaction was stirred at 55° C. for 3.25 h and then triethylamine (71.2 mL, 511 mmol) added keeping the temperature at less than 60° C. and the crystallisation held for 2 h at 50° C., cooled to 20° C. over 2 h, held at 20° C. for 2 days, filtered off, and washed with MeOH (2×100 mL) and dried in the vacuum oven at 50° C. to give the title compound (35.4 g, 81%).

$^1$H NMR (400 MHz, DMSO-d$_6$) δ ppm 13.43 (br. s., 1H), 11.36 (br. s., 1H), 8.61 (s, 1H), 8.09 (d, J=1.2 Hz, 1H), 7.92 (m, 1H), 7.51-7.46 (m, 2H), 7.32 (s, 1H), 7.28-7.22 (m, 2H), 6.61 (m, 1H), 4.09 (q, J=5.3 Hz, 1H), 3.73 (s, 2H), 3.18 (d, J=4.9 Hz, 3H), 2.60 (br. s., 1H), 2.56-2.40 (m, 4H), 0.94 (d, J=6.4 Hz, 6H).

Example 2

2-(6-(1H-Indol-4-yl)-1H-indazol-4-yl)-5-((4-isopropylpiperazin-1-yl)methyl)oxazole hemi-succinate

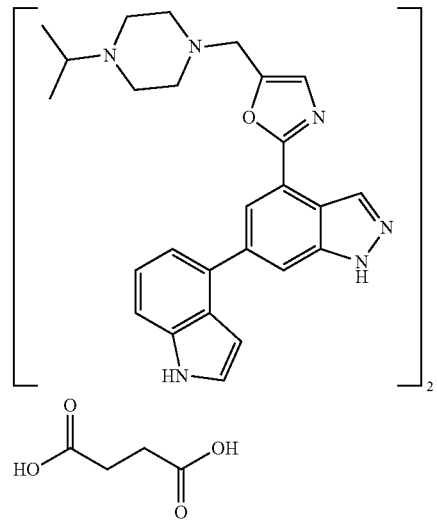

Method A 2-(6-(1H-Indol-4-yl)-1H-indazol-4-yl)-5-((4-isopropylpiperazin-1-yl)methyl)oxazole methanol solvate (729.1 g, 1.54 mol) and succinic acid (109.6 g, 0.93 mol) were dissolved in 10% w/w water in DMSO (4.35 L) at 85° C. The solution was filtered into another vessel, the line washed with hot 10% w/w water in DMSO (725 mL) and the solution kept at 85° C. Water (725 mL) was added maintaining the temperature at 85° C., then the contents were cooled to 40° C. over 2 h and the crystallisation seeded with 2-(6-(1H-indol-4-yl)-1H-indazol-4-yl)-5-((4-isopropylpiperazin-1-yl)methyl)oxazole hemi-succinate (3.63 g) slurried in 25% w/w water in DMSO (54 mL), followed by a line wash of 25% w/w water in DMSO (18.5 mL). The slurry was aged for 30 mins at 40° C. and then water (1.81 L) was added over 1 h, the contents stirred at 40° C. for 1 h, then the crystallisation cooled to 20° C. over 1 h, then aged for 17 h, filtered off, washed with 40% w/w water in DMSO (1.45 L), water (1.45 L), isopropanol (2×1.45 L) and dried under vacuum at 50° C. to give the title compound (626 g, 81%).

$^1$H NMR (400 MHz, DMSO-$d_6$) δ ppm 13.43 (1H, br s), 11.36 (1H, s), 10.00 (br. s, 1H) 8.60 (1H, d, J=0.9 Hz), 8.08 (1H, d, J=1.3 Hz), 7.90-7.92 (1H, m), 7.47-7.50 (1H, m), 7.47 (1H, t, J=2.8 Hz), 7.41 (1H, m), 7.24 (1H, t, J=7.3 Hz), 7.23 (1H, dd, J=7.3, 1.7 Hz), 6.59-6.62 (1H, m), 2.66 (1H, m), 2.40-2.61 (8H, m), 2.38 (2H, s), 1.22 (6H, d, J=6.5 Hz).

Method B 2-(6-(1H-Indol-4-yl)-1H-indazol-4-yl)-5-((4-isopropylpiperazin-1-yl)methyl)oxazole methanol solvate (10.0 kg, 21.2 mol) and succinic acid (1.50 kg, 12.7 mol) were dissolved in DMSO (50 L) at 85° C. The solution was filtered into another vessel, the line washed with hot DMSO (10 L) and the solution kept at 85° C. Water (17 L) was added maintaining the temperature at 82-88° C., then the contents were cooled to 40° C. at 0.2° C./min, and the crystallisation seeded with 2-(6-(1H-indol-4-yl)-1H-indazol-4-yl)-5-((4-isopropylpiperazin-1-yl)methyl)oxazole hemi-succinate (50 g) slurried in 25% w/w water in DMSO (500 mL), followed by a line wash of 25% w/w water in DMSO (500 mL). The slurry was aged for 30 mins then water (30 L) was added over 8 h, the contents stirred for 1 h, then the crystallisation cooled to 20° C. over 1 h, then aged for 14 h, filtered off, washed with 40% w/w water in DMSO (40 L), water (40 L), isopropanol (3×60 L) as slurry washes and dried under vacuum at 50° C. to give the title compound (7.25 kg, 68%).

$^1$H NMR (400 MHz, DMSO-$d_6$) δ ppm 13.43 (1H, br s), 11.36 (1H, s), 10.00 (br. s, 1H) 8.60 (1H, d, J=0.9 Hz), 8.08 (1H, d, J=1.3 Hz), 7.90-7.92 (1H, m), 7.47-7.50 (1H, m), 7.47 (1H, t, J=2.8 Hz), 7.41 (1H, m), 7.24 (1H, t, J=7.3 Hz), 7.23 (1H, dd, J=7.3, 1.7 Hz), 6.59-6.62 (1H, m), 2.66 (1H, m), 2.40-2.61 (8H, m), 2.38 (2H, s), 1.22 (6H, d, J=6.5 Hz).

Method C 2-(6-(1H-Indol-4-yl)-1H-indazol-4-yl)-5-((4-isopropylpiperazin-1-yl)methyl)oxazole methanol solvate (629.3 g, 1.33 mol) and succinic acid (94.4 g, 0.80 mol) were dissolved in DMSO (2.83 L) at 85° C. The solution was filtered into another vessel, washing the line with hot DMSO (629 mL) and the solution kept at 85° C. Water (1.132 L) was added maintaining the temperature at 85° C., then the contents were cooled to 70° C. over 1 h, and the crystallisation seeded with 2-(6-(1H-indol-4-yl)-1H-indazol-4-yl)-5-((4-isopropylpiperazin-1-yl)methyl)oxazole hemi-succinate (3.147 g) slurried in 25% v/v water in DMSO (31.5 mL), followed by a line wash of 25% w/w water in DMSO (31.5 mL). The slurry was aged for 120 mins then water (1.573 L) was added over 2.5 h, the contents stirred for 0.5 h, then the crystallisation cooled to 20° C. over 3 h, then aged for 17 h, filtered off, washing with 40% v/v water in DMSO (2.52 L), water (2.52 L), isopropanol (2×2.52 L) and dried under vacuum at 50° C. to give the title compound (501.4 g, 75%).

$^1$H NMR (700 MHz, DMSO-$d_6$) δ ppm 13.43 (1H, br s), 11.36 (1H, s), 10.00 (br. s, 1H) 8.60 (1H, d, J=0.9 Hz), 8.08 (1H, d, J=1.3 Hz), 7.90-7.92 (1H, m), 7.47-7.50 (1H, m), 7.47 (1H, t, J=2.8 Hz), 7.41 (1H, m), 7.24 (1H, t, J=7.3 Hz), 7.23 (1H, dd, J=7.3, 1.7 Hz), 6.59-6.62 (1H, m), 3.75 (2H, s), 2.66 (1H, m), 2.40-2.61 (8H, m), 2.38 (2H, s), 1.22 (6H, d, J=6.5 Hz).

Example 3

2-(6-(1H-Indol-4-yl)-1H-indazol-4-yl)-5-((4-isopropylpiperazin-1-yl)methyl)oxazole benzoate

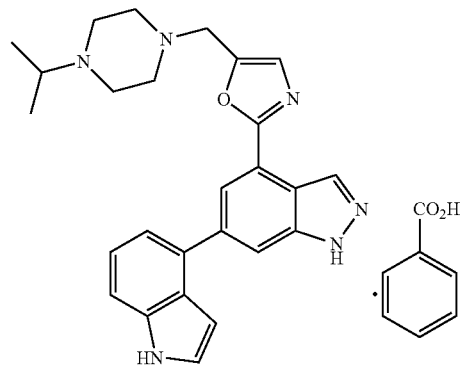

2-(6-(1H-Indol-4-yl)-1H-indazol-4-yl)-5-((4-isopropylpiperazin-1-yl)methyl)oxazole (28.55 g, 64.8 mmol) and benzoic acid (8.326 g, 68.2 mmol) were dissolved in DMSO (57 mL) and warmed to to 40° C. before adding isopropanol (57 mL). The crystallisation was seeded with 2-(6-(1H-indol-4-yl)-1H-indazol-4-yl)-5-((4-isopropylpiperazin-1-yl)methyl)oxazole benzoate* (183.6 mg) and stirred for 20 mins, isopropanol (114 mL) added, cooled to 20° C. and aged overnight, then filtered off, washed with isopropanol (171 mL) and dried under vacuum at 40° C. to give the title compound (25.95 g, 71%).

$^1$H NMR (400 MHz, DMSO-$d_6$) δ=13.41 (br. s., 1H), 11.36 (br. s., 1H), 8.60 (d, J=0.7 Hz, 1H), 8.08 (d, J=1.0 Hz, 1H), 8.00-7.86 (m, 3H), 7.64-7.57 (m, 1H), 7.52-7.45 (m, 5H), 7.32 (s, 1H), 7.28-7.21 (m, 2H), 6.61 (br. s., 1H), 3.74 (s, 2H), 2.63 (sept, J=6.6 Hz, 1H) 2.55-2.41 (m, 8H), 0.95 (d, J=6.6 Hz, 6H).

X-ray powder diffraction (XRPD) data were acquired on a PANalytical X'Pert Pro powder diffractometer, model PW3040/60 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a silicon wafer (zero background plate), resulting in a thin layer of powder.

The XRPD data for a polymorph of 2-(6-(1H-indol-4-yl)-1H-indazol-4-yl)-5-((4-isopropylpiperazin-1-yl)methyl)oxazole benzoate are shown in FIG. 1.

Characteristic XRPD angles and d-spacings for the solid state form are summarised in Table 1. Peak positions were measured using X'Pert Highscore software.

TABLE 1

| Diffraction Angles 2θ (°) | d-spacings (Å) |
|---|---|
| 6.7 | 13.2 |
| 8.7 | 10.1 |
| 11.2 | 7.9 |
| 11.6 | 7.6 |
| 12.9 | 6.9 |
| 13.3 | 6.6 |
| 16.2 | 5.5 |
| 17.5 | 5.1 |

TABLE 1-continued

| Diffraction Angles 2θ (°) | d-spacings (Å) |
|---|---|
| 18.7 | 4.7 |
| 19.8 | 4.5 |
| 20.0 | 4.4 |
| 21.0 | 4.2 |
| 22.0 | 4.0 |
| 22.4 | 4.0 |
| 25.6 | 3.5 |

*The 2-(6-(1H-indol-4-yl)-1H-indazol-4-yl)-5-((4-isopropylpiperazin-1-yl)methyl)oxazole benzoate seed was obtained in a salt screen which was performed as follows:
1. Dispense 750 μL of solvents into 2-mL HPLC vials containing 2-(6-(1H-indol-4-yl)-1H-indazol-4-yl)-5-((4-isopropylpiperazin-1-yl)methyl)oxazole (~20 mg)
2. Add stoichiometric amount of the acid to the vial
3. Stir the solutions/suspensions while cycling the temperature between 40° C. and 5° C. for 48 hours
4. Isolate crystalline solids by filtration
5. Samples that were solutions or non-crystalline products were subjected to rapid cooling at −20° C., then slow solvent evaporation at RT.

Specifically, the 2-(6-(1H-indol-4-yl)-1H-indazol-4-yl)-5-((4-isopropylpiperazin-1-yl)methyl)oxazole benzoate seed was obtained by adding acetonitrile as solvent to 2-(6-(1H-indol-4-yl)-1H-indazol-4-yl)-5-((4-isopropylpiperazin-1-yl)methyl)oxazole (19 mg) followed by one equivalent of benzoic acid in THF (3M).

The invention claimed is:

1. A process for preparing a compound of formula (IV) according to Scheme (I):

Scheme (I)

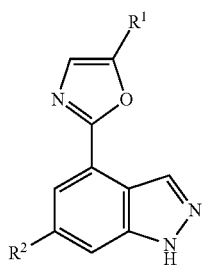

(IV)

wherein:
$R^1$ is

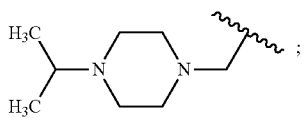

and
$R^2$ is

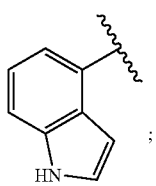

which process comprises the following steps:
(a) reacting a compound of formula (VII):

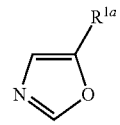

(VII)

or a salt thereof,
wherein:
$R^{1a}$ is

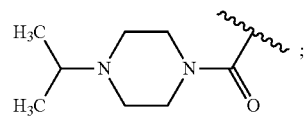 [SMILES: *C(=O)N1CCN(C(C)C)CC1]

with a compound of formula (X):

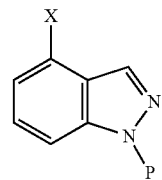

(X)

or a salt thereof,
wherein:
X is halogen; and
P is tetrahydro-2H-pyran-2-yl;
in the presence of a palladium catalyst, to give a compound of formula (XI):

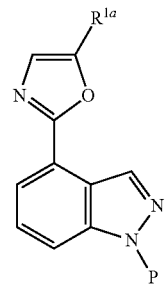

(XI)

or a salt thereof,
wherein:
$R^{1a}$ is

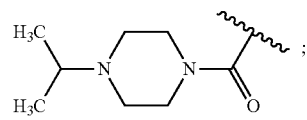

and

P is tetrahydro-2H-pyran-2-yl;

(b) reacting the compound of formula (XI) above, or a salt thereof, with pinacolborane in the presence of (1,5-cyclooctadiene)(methoxy)iridium (I) dimer, to give a compound of formula (XII):

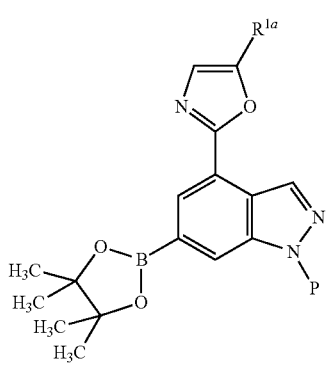
(XII)

or a salt thereof,
wherein:
R$^{1a}$ is

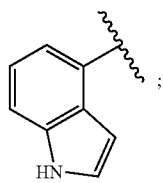 [SMILES: *c1cccc2[nH]ccc12]

and

P is tetrahydro-2H-pyran-2-yl;

(c) reacting the compound of formula (XII) above, or a salt thereof, with a compound of formula (XIV):

R$^2$—X$^1$ (XIV)

or a salt thereof,
wherein:
R$^2$ is

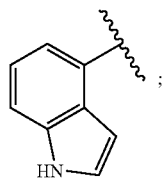

and

X$^1$ is halogen;

in the presence of a palladium catalyst, to give a compound of formula (XIII):

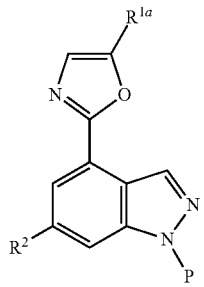
(XIII)

wherein:
R$^{1a}$ is

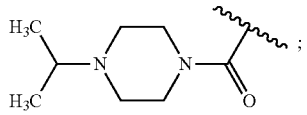

R$^2$ is

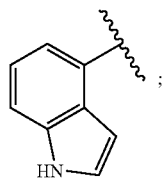

and

P is tetrahydro-2H-pyran-2-yl; and (d) reacting the compound of formula (XIII) above with a reducing agent selected from the group consisting of sodium borohydride, lithium aluminum hydride, diisobutyl aluminum hydride and sodium bis(2-methoxyethoxy)aluminum hydride, followed by deprotection, to give the compound of formula (IV) above; or A process for preparing a compound of formula (IV) according to Scheme (II):

Scheme (II)

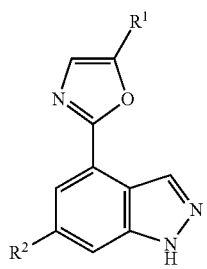
(IV)

wherein:
R¹ is

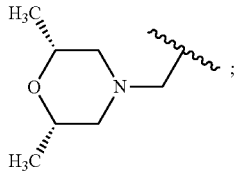

and
R² is

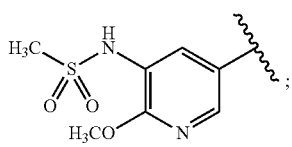 [SMILES: *c1cnc(OC)c(NS(C)(=O)=O)c1]

which process comprises the following steps:
(a) reacting a compound of formula (VII):

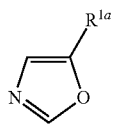

(VII)

or a salt thereof,
wherein:
R¹ᵃ is

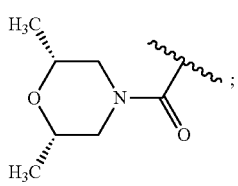

with a compound of formula (X):

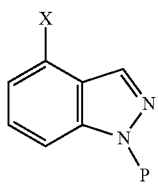

(X)

or a salt thereof,
wherein:
X is halogen; and
P is tetrahydro-2H-pyran-2-yl;
in the presence of a palladium catalyst, to give a compound of formula (XI):

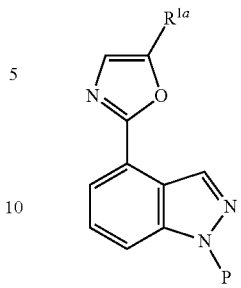

(XI)

or a salt thereof,
wherein:
R¹ᵃ is

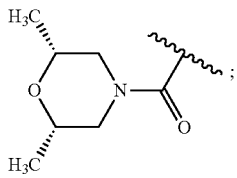

and
P is tetrahydro-2H-pyran-2-yl;
(b) reacting the compound of formula (XI) above, or a salt thereof, with pinacolborane in the presence of (1,5-cyclooctadiene)(methoxy)iridium (I) dimer, to give a compound of formula (XII):

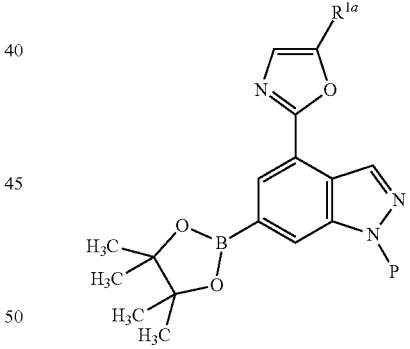

(XII)

or a salt thereof,
wherein:
R¹ᵃ is

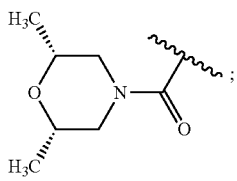 [SMILES: *C(=O)N1C[C@@H](C)O[C@@H](C)C1]

and
P is tetrahydro-2H-pyran-2-yl;
(c) reacting the compound of formula (XII) above, or a salt thereof, with a compound of formula (XIV):

$$R^2—X^1 \quad (XIV)$$

or a salt thereof,
wherein:
R² is

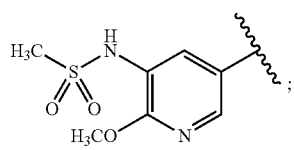 [SMILES: *c1cnc(OC)c(NS(C)(=O)=O)c1]

and
X¹ is halogen;
in the presence of a palladium catalyst, to give a compound of formula (XIII):

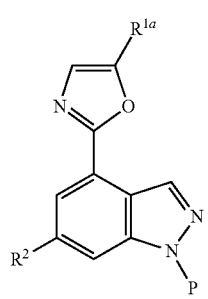

(XIII)

wherein:
R^{1a} is

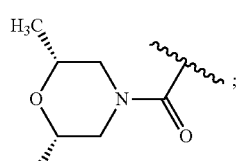

R² is

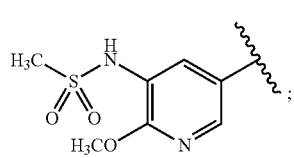

and
P is tetrahydro-2H-pyran-2-yl; and
(d) reacting the compound of formula (XIII) above with a reducing agent selected from the group consisting of sodium borohydride, lithium aluminum hydride, diisobutyl aluminum hydride and sodium bis(2-methoxyethoxy)aluminum hydride, followed by deprotection, to give the compound of formula (IV) above.

2. The process according to claim 1, wherein:
R¹ is

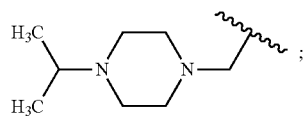

and
R² is

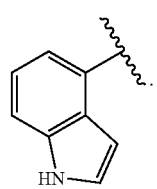 [SMILES: *c1cccc2[nH]ccc12]

3. The process according to claim 1, wherein:
R¹ is

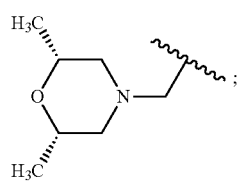

and
R² is

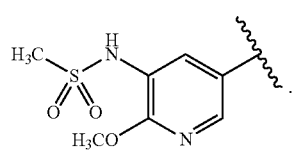

4. The process according to claim 1, wherein the reducing agent is lithium aluminium hydride.

5. The process according to claim 1, wherein X is chlorine.

6. The process according to claim 1, wherein X¹ is chlorine.

7. The process according to claim 1, wherein deprotection is performed under acidic conditions.

* * * * *